(12) United States Patent
Nestenborg (10) Patent No.: US 8,052,673 B2
(45) Date of Patent: Nov. 8, 2011

(54) FOLDED CATHETER ASSEMBLY WITH ADHESIVE GRIP

(75) Inventor: Daniel Nestenborg, Frölunda (SE)

(73) Assignee: Astra Tech AB, Molndal (SE)

( * ) Notice: Subject to any disclaimer, the term of this patent is extended or adjusted under 35 U.S.C. 154(b) by 155 days.

(21) Appl. No.: 11/597,471

(22) PCT Filed: Jul. 15, 2005

(86) PCT No.: PCT/SE2005/001158
§ 371 (c)(1),
(2), (4) Date: Nov. 22, 2006

(87) PCT Pub. No.: WO2006/009509
PCT Pub. Date: Jan. 26, 2006

(65) Prior Publication Data
US 2008/0200907 A1 Aug. 21, 2008

(30) Foreign Application Priority Data
Jul. 16, 2004 (SE) ........................ 0401879

(51) Int. Cl.
*A61M 27/00* (2006.01)
(52) U.S. Cl. ........ 604/544; 604/171; 604/172; 604/199; 206/364; 206/210; 206/570; 206/571; 206/572; 206/219; 206/438; 206/439; 383/38; 383/39; 383/40

(58) Field of Classification Search ................. 604/171, 604/172, 199, 544
See application file for complete search history.

(56) References Cited

U.S. PATENT DOCUMENTS
3,146,884 A 9/1964 Pereny et al.
(Continued)

FOREIGN PATENT DOCUMENTS
DE 2227 416 A 12/1972
(Continued)

OTHER PUBLICATIONS
Database WPI, Week 199747, Derwent Publications Ltd., London, GB, AN 1997-506803 & JP 9238952 A (Daiei K), Sep. 16, 1997.

*Primary Examiner* — Tatyana Zalukaeva
*Assistant Examiner* — Ilya Treyger
(74) *Attorney, Agent, or Firm* — Birch, Stewart, Kolasch & Birch, LLP (57) ABSTRACT

A catheter assembly is disclosed comprising a catheter and a receptacle enclosing said catheter. The receptacle has a first part and a second part, which parts are foldable over each other. Further, at least one sticky adhesive area is arranged on the surface of one of the parts of the receptacle in such a way that the sticky adhesive area is covered by the other part when the receptacle is in a folded disposition, and exposed to the environment when the receptacle is in an unfolded disposition.

15 Claims, 5 Drawing Sheets

U.S. PATENT DOCUMENTS

| | | | | |
|---|---|---|---|---|
| 3,420,433 A | * | 1/1969 | Bostwick | 229/80 |
| 3,537,451 A | * | 11/1970 | Beck et. al. | 604/165.03 |
| 3,680,772 A | | 8/1972 | Hoover | |
| 4,055,682 A | * | 10/1977 | Merrill | 427/2.1 |
| 4,091,922 A | | 5/1978 | Egler | |
| 4,754,877 A | * | 7/1988 | Johansson et al. | 206/364 |
| D300,947 S | * | 5/1989 | Utas-Sjoberg | D24/118 |
| 5,100,689 A | * | 3/1992 | Goldberg et al. | 600/36 |
| 5,165,540 A | * | 11/1992 | Forney | 206/364 |
| 6,004,305 A | * | 12/1999 | Hursman et al. | 604/328 |
| D498,672 S | * | 11/2004 | Nestenborg | D9/415 |
| D499,335 S | * | 12/2004 | Nestenborg | D9/722 |
| 2003/0168365 A1 | * | 9/2003 | Kaern | 206/364 |
| 2006/0263404 A1 | * | 11/2006 | Nielsen et al. | 424/422 |

FOREIGN PATENT DOCUMENTS

| | | |
|---|---|---|
| GB | 2 006 716 A | 5/1979 |
| WO | WO 86/06264 A1 | 11/1986 |
| WO | WO 96/30277 A1 | 10/1996 |
| WO | WO-98/11932 A1 | 3/1998 |
| WO | WO 03/064279 A1 | 8/2003 |

\* cited by examiner

FOLDED CATHETER ASSEMBLY WITH ADHESIVE GRIP

FIELD OF THE INVENTION

The present invention relates to a catheter assembly and a method for producing such a catheter assembly.

BACKGROUND OF THE INVENTION

Catheters find their use in many different medical applications, such as urinary catheters for bladder drainage. Each catheter is normally pre-packed in a receptacle by the manufacturer, in order to maintain the catheter in a clean and preferably sterile condition.

A urinary catheter in general need to have a lubricant applied to the outer surface thereof to facilitate insertion into the urethra. Especially, for lubrication purposes, a hydrophilic urinary catheter may have a hydrophilic outer surface coating or layer which should be wetted by a fluid such as water for a certain time period prior to insertion of the catheter into the urethra of a patient. In order to facilitate the use and to improve cleanliness of the catheter, the assemblies have in recent years developed to comprise a rupturable wetting fluid pouch or container as well. Such assemblies are disclosed in e.g. WO 97/26937, WO 01/43807 and WO 98/11932.

However, a common problem for most known catheter assemblies is that they are rather complicated to handle. For example, the handling requires normally opening the sealed package by peeling or tearing, introducing a wetting fluid into the package by pouring water into an opening or opening a wetting fluid container already present within the package, holding the package during the activation period, which is typically about 30 seconds, extracting the wetted catheter and introducing it into the urethra, and all preferably without spilling the released liquid. Further, it could also be necessary that the catheter is reintroduced into the package after use for disposal of the catheter. This could naturally be difficult for any patient, and for the patients being e.g. paraplegics or disabled, the task becomes particularly demanding. Further, water on the receptacle surface or on the patients fingers normally makes the receptacle slippery, which makes proper handling even more problematic.

In order to facilitate the handling of the catheter assemblies, it has been proposed in the art to use a small area of sticky adhesive on the outer surface of the receptacle, close to one of the corners. Said sticky adhesive is during storage protected by a protective sheet. In the use situation the sheet is removed, and the adhesive could then be used for holding the receptacle onto a wall or the like. Such catheter assemblies are e.g. disclosed in WO 03/064279 and U.S. Pat. No. 5,895,374.

However, in practice these known measures have proven insufficient and inadequate to effectively alleviate the above-related handling problems. Still further, the protective sheet need to be small and relatively firmly adhered to the sticky adhesive in order not to fall off involuntarily during production, storage and transportation. However, this requirement makes the operation of removing the protective sheet upon use in itself a rather tedious and cumbersome task for the user. Further, there is still an unavoidable risk that the protective sheet will fall of unintentionally. If this happens during production, which it in practice often does, it will normally result not only in damaged products, but also in significant disturbances in the production process and contamination of the production site, which of course incurs greater production costs etc. Accordingly, a proper compromise between an adequate fastening of the protective sheet and an easy removal of the same has proven difficult, if not impossible, to achieve.

Accordingly, there is still a need for an improved catheter assembly which alleviates the above-discussed problems of the prior art.

SUMMARY OF THE INVENTION

It is a general object of the present invention to alleviate the above-discussed problems.

This object is achieved with a catheter assembly and a production method according to the appended claims.

According to a first aspect, there is provided a catheter assembly comprising: a catheter; a receptacle enclosing said catheter, the receptacle having a first part and a second part, said parts being foldable over each other; and at least one sticky adhesive area arranged on the surface of one of the parts of the receptacle in such a way that the sticky adhesive area is covered by the other part when the receptacle is in a folded disposition, and exposed to the environment when the receptacle is in an unfolded disposition.

By means of the invention, the foldable receptacle functions as a cover for the sticky adhesive area, thereby avoiding the need for any additional protective sheet or the like. The number of separate components of the assembly is hereby reduced, making the production and assembly process simpler and more cost effective. Further, the number of separate waste items to be taken care of after use is limited, thereby facilitating the handling of the device, which is especially important for handicapped users. The total quantity of waste material could also be limited.

Further, the foldable construction enables a facilitated activation and exposure of the sticky adhesive area, by allowing larger unfolding tabs etc. Hereby the use of the catheter assembly is greatly facilitated, especially for disabled users, such as paraplegics. In addition, the folded construction enables a larger sticky adhesive area, without making the assembly more cumbersome to use.

In addition, the folded construction enables a more flexible placement of the sticky adhesive area on the product, thereby improving the functionality of said area in use. For example, the sticky area could be placed in a position enabling a use both as fastening means for holding the assembly towards a wall, a sink or the like during preparation and activation of the catheter, during use, during return of the catheter into the receptacle for disposal, etc. In alternatively, or preferably in addition, the sticky area could be arranged in a position in a gripping portion of the receptacle, thereby providing an enhanced grip for the user's hand when handling and manipulating the receptacle.

Still further, the folded receptacle enables a more compact product, being easier and more cost effective to handle before use. The folded receptacle also becomes more stable, which facilitates handling and use of the product.

The assembly is particularly useful for urinary catheters, and preferably urinary catheters intended for intermittent use.

Preferably, the assembly further comprises a wetting fluid, wherein the catheter has on at least part of its surface a hydrophilic surface layer providing low-friction surface character of the device by treatment with said wetting fluid. Such an assembly requires a more cumbersome handling before use, making the enhanced gripping and fastening of the inventive assembly even more useful. Most preferably, the assembly presents a storage state in which the wetting fluid is kept separated from the hydrophilic surface layer of the catheter, and an activation state in which the wetting fluid is brought into contact with said hydrophilic surface layer before an intended use of the catheter, wherein the catheter is arranged in one of the parts of the receptacle, whereas the wetting fluid is arranged in the other part. For such an assembly, the foldable assembly provides a very compact and useful catheter product.

The sticky adhesive area is preferably relatively large, e.g. having an extension exceeding 1 cm$^2$, and preferably exceeding 2 cm$^2$, and most preferably exceeding 3 cm$^2$. It is also possible to use several sticky adhesive areas. If several sticky adhesive areas are used, they could either be arranged solely on one of the parts, or be arranged on both parts of the receptacle. By arranging the sticky adhesive areas on both parts, a wider distribution of the sticky adhesive areas in the unfolded disposition could be accomplished, thereby improving the usability even further.

The part of the receptacle covering the adhesive area in the folded disposition, and being exposed to the environment when the receptacle is in an unfolded disposition, is preferably arranged to be less adherent to the adhesive forming the adhesive area than the corresponding part on which the sticky adhesive area is arranged. This could be accomplished by a suitable choice of adhesive, materials in the receptacle, roughness of the surfaces, etc. However, in a preferred embodiment, the part being arranged to be less adherent to the adhesive comprises a coating or layer of a material to which the adhesive area adheres relatively loosely, said coating/layer being arranged to cover at least a part of the adhesive area in the folded disposition. By means of the above-discussed arrangement, the assembly may be optimized so that the assembly is easy to unfold, and at the same time provides a strong bond to a wall, sink or the like.

According to a second aspect of the invention, there is provided a method of producing a catheter assembly, comprising the steps: providing a catheter; enclosing the catheter in a receptacle; arranging at least one sticky adhesive area on the surface of a first part of the receptacle; and folding a second part of the receptacle over the first part in such a way that the sticky adhesive area becomes covered by the second part.

Similar advantages are provided by this aspect of the invention as already discussed in view of the previous aspects of the invention.

These and other aspects of the inventive concept will be apparent from and elicited with reference to the embodiments described hereinafter.

BRIEF DESCRIPTION OF THE DRAWINGS

By way of example embodiments of the invention will now be described with reference to the accompanying drawings in which.

DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter, the dimensions of the fluid compartments, etc.

Hydrophilic catheters may be used for many different purposes, and for insertion into various types of body-cavities. However, the following discussion is in particular concerned with the preferred field of use, urinary catheters, even though the invention is not limited to this particular type of catheters.

Figure 1:
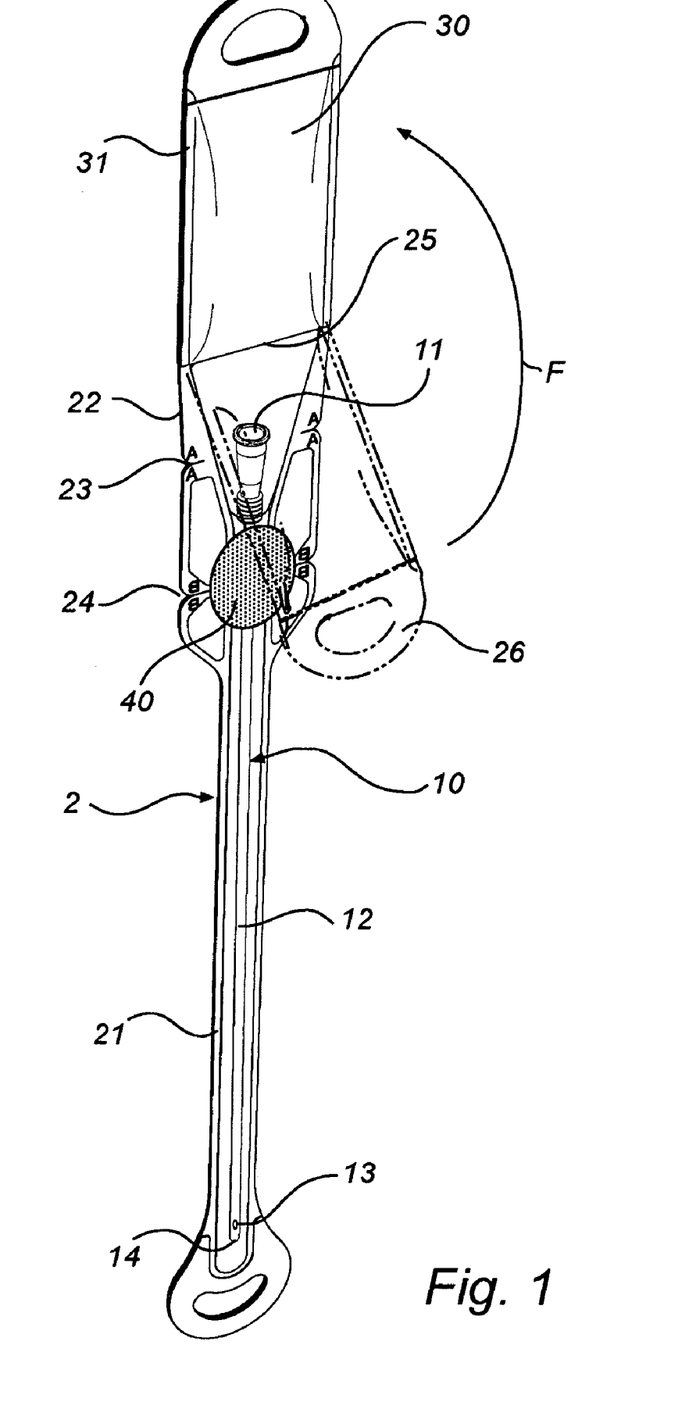
FIG. 1 illustrates a first embodiment of a catheter assembly according to the invention.

A catheter 10 as illustrated in the drawings, e.g. in FIG. 1, comprises a flared rearward portion 11 and an elongate shaft or tube 12 projecting forwardly from the rearward portion 11. An open-ended internal lumen (not shown) extends from the rear end of the rearward portion 11 to a drainage aperture 13 in a rounded tip 14 of the elongate tube 12. The rearward portion 11 may function as a connector of the catheter 10, being connectable to other devices, such as a urine collection bag, a drainage tube or the like.

At least a part of the elongate tube 12 forms an insertable length to be inserted through a body opening of the user, such as the urethra in case of a urinary catheter. By insertable length is normally, in the context of a hydrophilic catheter, meant that length of the elongate tube 12 which is coated with a hydrophilic material, for example PVP, and which is insertable into the urethra of the patient. Typically, this will be 80-140 mm for a female patient and 200-350 mm for a male patient. Several different types of hydrophilic polymer coating are feasible, as is per se known in the art. However, a preferred hydrophilic polymer is polyvinylpyrrolidone.

The substrates may be made from any polymer material, which are well-known in the technical field and to which the said hydrophilic polymers adhere, such as polyurethanes, latex rubbers, other rubbers, polyvinylchloride, other vinyl polymers, polyesters and polyacrylates.

With reference to FIG. 1, a first embodiment of a catheter assembly comprises a wetting receptacle or receptacle 2, preferably of a transparent flexible plastics material, and a catheter 10 arranged therein. The receptacle 2 has an elongate pocket 21 at its forward end, and close to its rearward end 22 the receptacle presents means 22, 23 for opening the receptacle, such as tear lines or the like, as is per se well known in the art. Further opening means may be arranged at the forward or rearward end. The wetting receptacle 20 is adapted for accommodation of at least the insertable length of the catheter tube 12 in the elongate pocket 21.

The catheter assembly further comprises a hydrophilic urinary catheter 10, as is discussed in more detail in the foregoing.

The catheter assembly according to this embodiment also comprises a wetting fluid 30 arranged at the rearward end. The wetting fluid is here provided separated from the hydrophilic surface of the catheter during storage, in a separate wetting fluid compartment 31. The wetting fluid is intended to wet the hydrophilic surface coating, thereby to produce the low-friction character of the same. A suitable wetting fluid for most hydrophilic coatings could typically be sterile water or saline. In the embodiments of e.g. FIG. 1, the wetting fluid is kept separated from the catheter in a compartment which is openable in order to enable activation of the catheter assembly. Thus, the activation is performed by opening the compartment and releasing the wetting fluid into the receptacle holding the catheter so that it comes into contact with the hydrophilic coating of the catheter. The wetting fluid compartment could be a separate container, or an integrated compartment of the receptacle. The compartment may be openable by means of pressing, tearing, piercing, twisting, etc, which is per se well-known in the art.

However, alternatively the wetting fluid could be arranged in direct contact with the hydrophilic coating, thus maintaining the coating in a constantly activated state (not shown), as is per se known in the art.

The receptacle comprises two parts being foldable relative to each other along a folding line 25. In this embodiment, the folding line is arranged between the part of the receptacle housing the catheter and the part housing the wetting fluid. Accordingly, the rearward portion of the receptacle housing the wetting fluid could be folded down over the forward part of the receptacle housing the catheter to a folded disposition, as is illustrated by broken lines in FIG. 1.

Further, the assembly comprises a sticky adhesive area 40, which is arranged on the receptacle in such a way that it is between the parts when the receptacle is in its folded disposition. When the folded parts are unfolded to the unfolded disposition, as is illustrated by arrow F in FIG. 1, the sticky adhesive area becomes exposed to the environment, thereby making it useful in as an aid for improved gripping and fastening of the assembly.

The folded parts preferably extends past the sticky adhesive area, seen in the direction from the folding line, thereby providing gripping tabs 26 for facilitating unfolding of the receptacle upon use.

The sticky adhesive area 40 is preferably a hot melt glue, which is arranged on the receptacle in a warm and melted condition, and which adheres to the receptacle surface when it cools down. For example, the commercially available RP51™ from Raflatac or Sanicare™ from Henckel could be used. However, other type of adhesives or sticky means may be used as well. For example, it is possible to use double-stick tape or the like.

The stickiness of the adhesive area is preferably chosen to be high enough to provide a good grip for the user and an adequate holding of the device during use against e.g. a sink or a wall, but at the same time low enough to enable an easy unfolding and exposure of the sticky area during activation of the product, even for handicapped users, and to enable loosening of the device after use or for rearrangement A measure of the stickiness of an adhesive is the shear strength, i.e. the force required to exert in a direction along the adhesive area in order to loosen the fastening provided by the adhesive. The adhesive has preferably a shear strength in the range 0.1-2.0 $N/cm^2$, and most preferably in the range 0.1-0.5 $N/cm^2$. However, the optimal stickiness is dependent on the extension area of the adhesive area, the size and weight of the product, etc. Typically, a lower stickiness would be required when the extension area of the adhesive area is large, whereas a higher stickiness would be needed when the extension area is smaller.

The adhesive area preferably has an extension exceeding 1 $cm^2$, and preferably exceeding 2 $cm^2$, and most preferably exceeding 3 $cm^2$. In some embodiments the sticky area could cover the whole area enclosed by the foldable parts, and e.g. in such embodiments, the adhesive area may be as large as 10 $cm^2$ or more.

In order to facilitate unfolding, the sticky adhesive area is preferably arranged to be more strongly adhered to one of the parts than the other. This could be accomplished in various ways, such as in the preparation and choosing of the adhesive material, or by using a suitable method for arranging the adhesive between the folded parts. However, alternatively or additionally, it may also be accomplished by the use of different receptacle materials facing the sticky adhesive area. For example, most adhesives adheres more strongly to PET than to PE.

The choice of adhesive and materials are preferably made in order to fulfill the following conditions:

The adhesive should preferably be more strongly adhered to the one part where it is intended to be maintained after unfolding, than to the other part, covering it in the folded disposition.

The adhesive should preferably not be too strongly adhered to this other part, thereby enabling an easy and convenient loosening during the unfolding.

The adhesive should preferably adhere relatively strongly to the wall, sink or the like, in order to provide a convenient activation and use of the catheter assembly.

The above-mentioned conditions may be obtained by an adequate choice of materials, adhesive, and the like. However, it is also possible to arrange a layer or coating on the covering part, i.e. the part to be loosened from the adhesive during the unfolding. This layer or coating preferably has low-friction properties and low adherence to the adhesive, and is preferably arranged to cover at least a part of the area with which the adhesive is in contact in the folded disposition. This coating or layer could e.g. comprise a layer of PE material, a silicone coating or the like.

Figure 2:
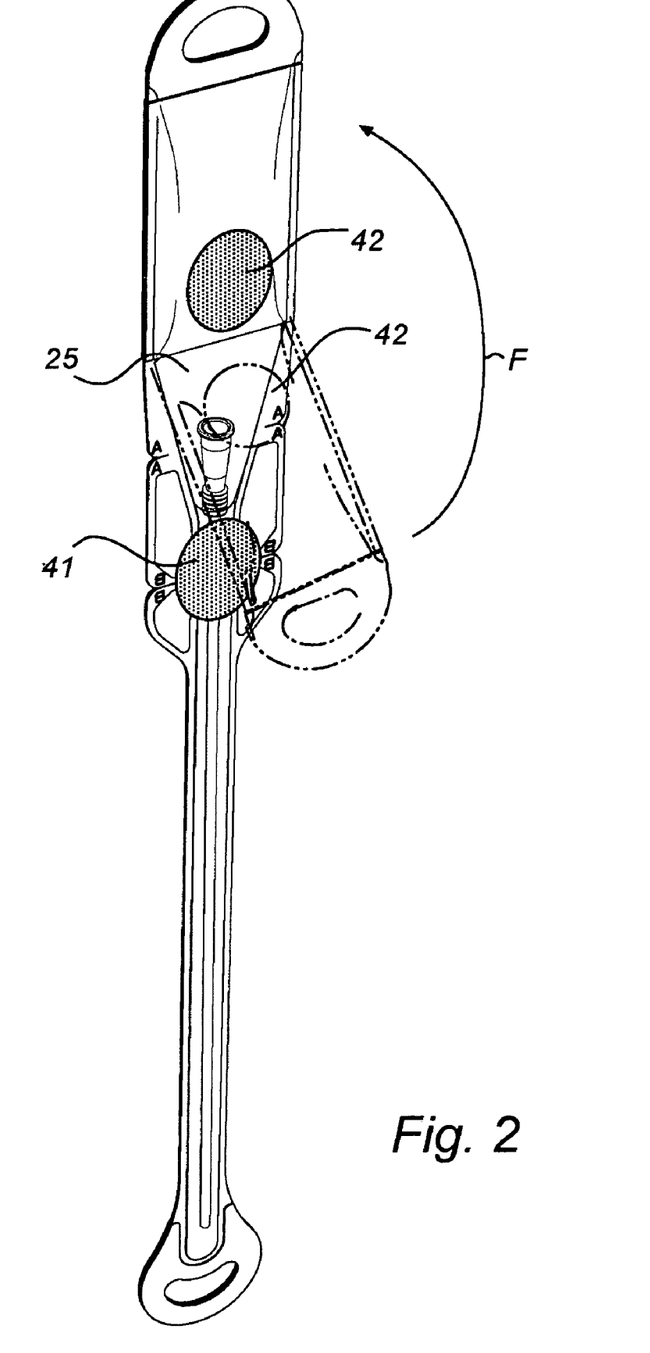
FIG. 2 illustrates a second embodiment of a catheter assembly according to the invention.

The second embodiment illustrated in FIG. 2 generally resembles the assembly according to the first embodiment, as discussed above in relation to FIG. 1. However, in the second embodiment two separate sticky adhesive area 41 and 42 are used, and arranged between the foldable parts of the receptacle. These separate sticky adhesive areas may be arranged on the same part of the receptacle. However, in the illustrated embodiment, one sticky adhesive area 41 is arranged on the forward part, i.e. arranged to adhere more strongly to said part, and one sticky adhesive area 42 is arranged on the rearward part, i.e. arranged to adhere more strongly to said part. With this arrangement, the sticky adhesive areas will become more distributed in the unfolded disposition than in the folded disposition of the receptacle, i.e. the distance between the sticky adhesive areas will increase when unfolding the assembly.

Figure 3A:
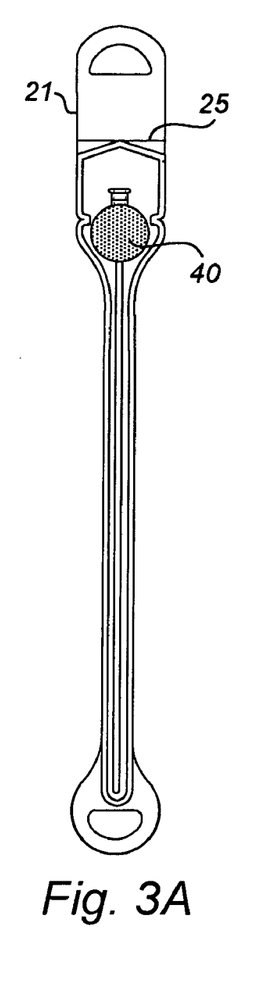
FIG. 3A illustrates a third embodiment of a catheter assembly according to the invention.
Figure 3B:
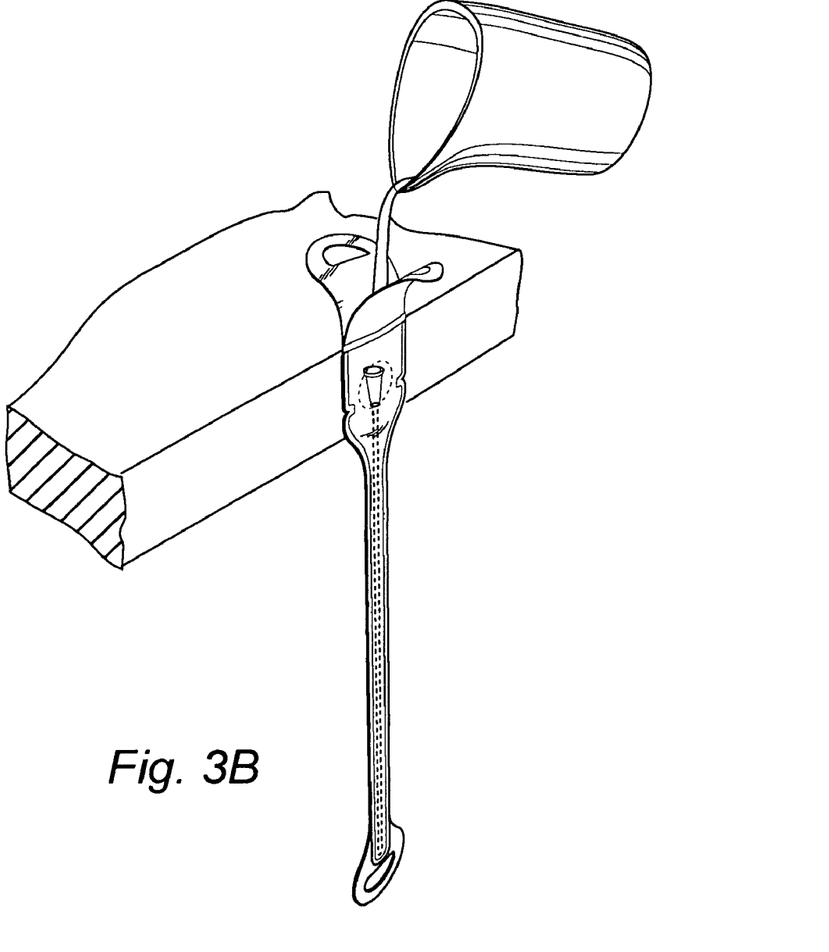
FIG. 3B illustrates the third embodiment in a use situation when adhered to a table top.

A third embodiment of the assembly is illustrated in FIGS. 3A and 3B. In this embodiment, the assembly comprises no wetting fluid. The folding line 25 is preferably arranged above the catheter, thereby avoiding bending of the catheter shaft, and the rearward part 22' is large enough to cover the sticky adhesive area 40 when in the folded disposition.

In use, the sticky adhesive area may be used for fastening the assembly to an external object, such as a table top. Such a situation is illustrated in FIG. 3B. Hereby, handling of the assembly is facilitated. For example, the assembly may be fastened to the external object when pouring water into the assembly for wetting of the catheter, when extracting the catheter for use, when retracting the catheter into the receptacle for disposal, etc.

Figure 4:
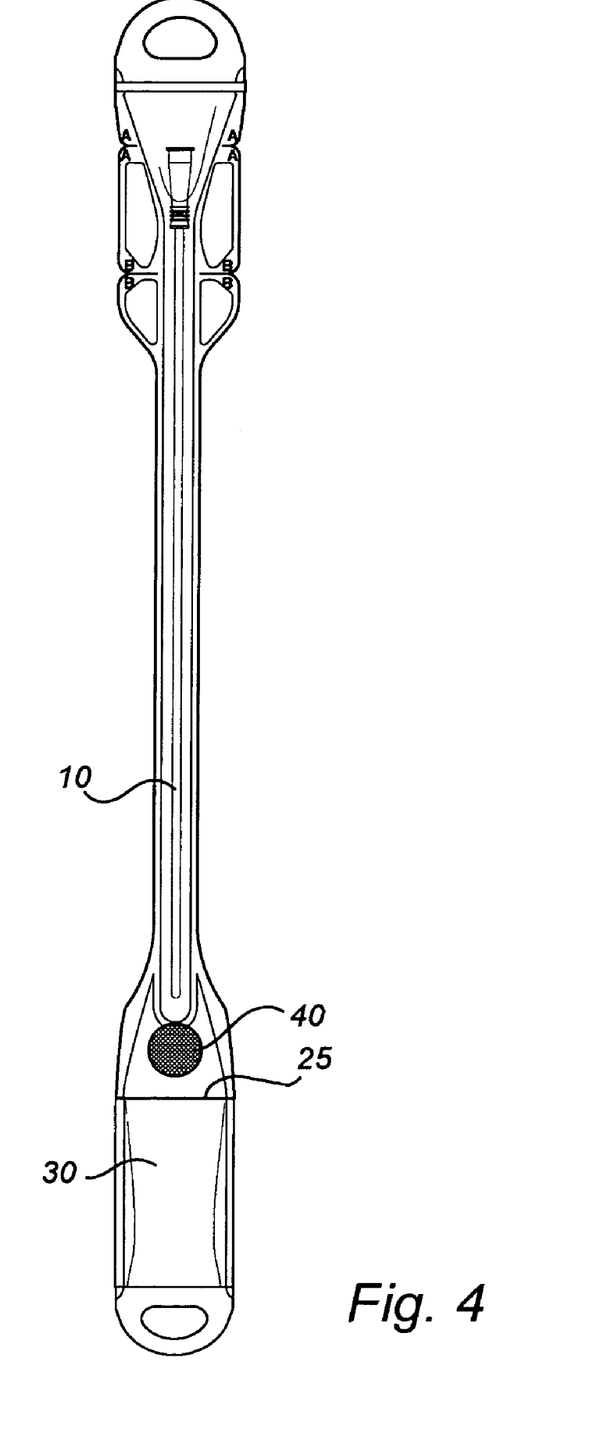
FIG. 4 illustrates a fourth embodiment of a catheter assembly according to the invention.

In an alternative embodiment, illustrated in FIG. 4, the catheter and the wetting fluid are switched in comparison with the embodiments as discussed previously with reference to FIGS. 1 and 2. Consequently, the catheter 10 is arranged in a rearward part, and the wetting fluid 30 in a forward part, whereby the distal end of the catheter is closest to the wetting fluid, and the proximal end farthest from the wetting fluid. The folding line 25 is still arranged between the catheter and the wetting fluid, and the sticky adhesive area 40 is arranged is such a position that it is covered by the receptacle part in the folded disposition.

Figure 5:
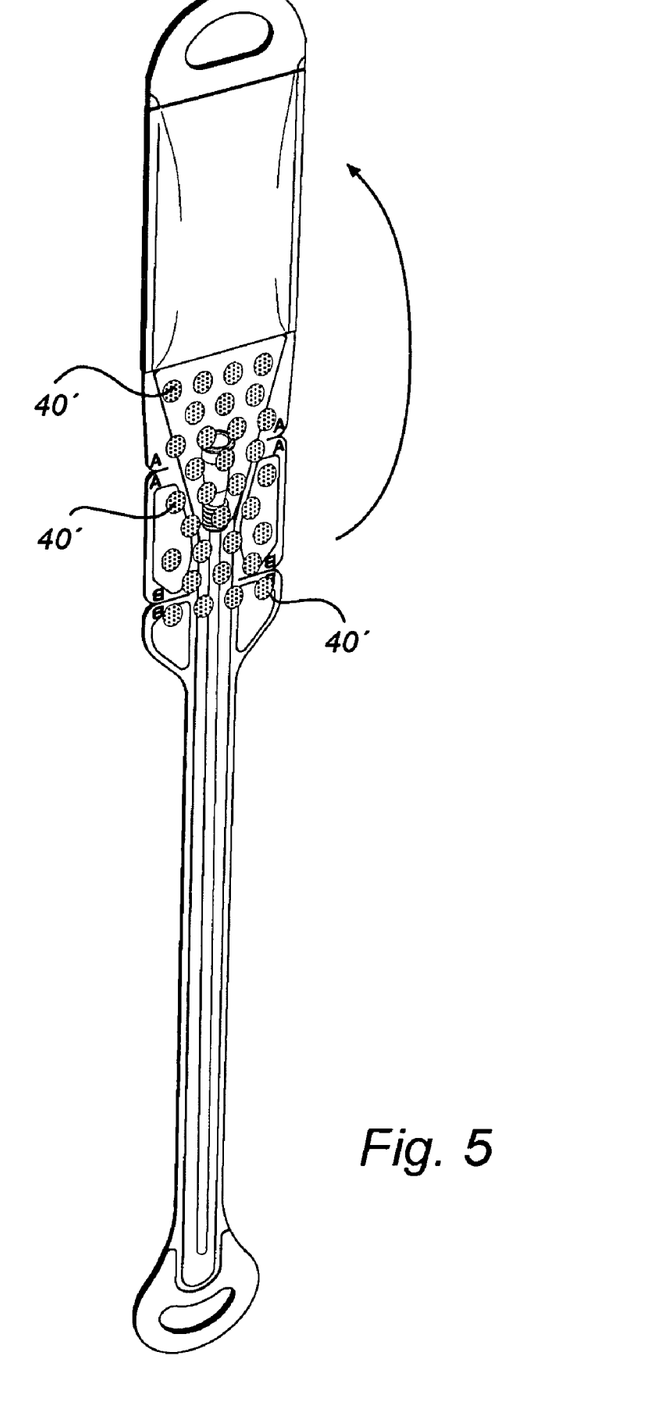
FIG. 5 illustrates a fifth embodiment of a catheter assembly according to the invention.

In still another embodiment, illustrated in FIG. 5, a plurality of sticky adhesive areas 40' are used, and arranged distributed on the receptacle. Preferably, the sticky adhesive areas are distributed over essentially the whole area being between the foldable parts when the receptacle is in the folded disposition.

The invention has now been discussed in relation to different embodiments. However, it should be appreciated by those versed in the art that several further alternatives are possible. For example, the features of the different embodiments discussed above may naturally be combined in many other ways.

It is further possible to use the invention for other types of catheters than urinary catheters, such as vascular catheters or the like. Still further, it is possible to arrange the wetting fluid container in many different ways. For example, the container may be a separate container, but forming part of the assembly. Such a wetting fluid container may be arranged completely inside the receptacle, partly inside the receptacle, or completely outside the receptacle. Alternatively, the wetting fluid container may be an integrated compartment of the receptacle. This compartment may be separated from the compartment housing the insertable part of the catheter, or be integrated with such a compartment. In the latter case, the catheter may be maintained in a wetted, activated state.

Further, the wetting fluid container may be arranged close to the distal part of the catheter, close to the proximal part of the catheter, or in any other suitable location in the assembly. In case the wetting fluid is arranged separately from the insertable part of the catheter, the separation wall or joint could e.g. be a breakable or peelable membrane wall, but alternative embodiments are naturally feasible, such as various types of detachable or openable caps or closings. The wetting fluid container may be arranged to be discharged upon application of a twist, a compression, a pull or the like on the fluid container. Preferably the wetting fluid may be discharged without breaking or rupturing the receptacle, even though this may not be necessary, depending on the intended use, etc.

Many different materials could also be used for the different parts of the catheter assembly.

It will be appreciated by those versed in the art that several such alternatives similar to those described above could be used without departing from the spirit of the invention, and all such modifications should be regarded as a part of the present invention, as defined in the appended claims.

The invention claimed is:

1. A catheter assembly comprising:
a catheter;
a closed receptacle enclosing said catheter, the receptacle having a first compartment and a second compartment separated from the first compartment by a fold line, said first and second compartments being foldable over each other while the receptacle is maintained in a closed state; and
at least one sticky adhesive area arranged on the surface of one of the first and second compartments of the receptacle in such a way that the sticky adhesive area is covered by the other of the first and second compartments when the receptacle is in a folded disposition, and exposed to the environment when the receptacle is in an unfolded disposition.

2. The assembly of claim 1, wherein the catheter is a urinary catheter, and preferably intended for intermittent use.

3. The assembly of claim 1, further comprising a wetting fluid provided in one of the first and second compartments of the receptacle, wherein the catheter has on at least part of its surface a hydrophilic surface layer providing low-friction surface character of the device by treatment with said wetting fluid.

4. The assembly of claim 3, wherein the receptacle provides a storage state in which the wetting fluid is kept separated from the hydrophilic surface layer of the catheter, and an activation state in which the wetting fluid is brought into contact with said hydrophilic surface layer before an intended use of the catheter.

5. The assembly of claim 4, wherein the catheter is arranged in the other of first and second compartments of the receptacle.

6. The assembly of claim 1, wherein the at least one sticky adhesive area has an extension exceeding 1 cm$^2$.

7. The assembly of claim 1, wherein the assembly comprises several sticky adhesive areas.

8. The assembly of claim 7, wherein at least one of the sticky adhesive areas is arranged on each part of the receptacle.

9. The assembly of claim 1, wherein the compartment of the receptacle covering the adhesive area in the folded disposition, and being exposed to the environment when the receptacle is in an unfolded disposition, is arranged to be less adherent to the adhesive forming the adhesive area than the corresponding compartment on which the sticky adhesive area is arranged.

10. The assembly of claim 9, wherein the compartment being arranged to be less adherent to the adhesive comprises a coating or layer of a material to which the adhesive area adheres relatively loosely, said coating/layer being arranged to cover at least a part of the adhesive area in the folded disposition.

11. A method of producing a catheter assembly, comprising the steps:
providing a catheter;
providing a wetting fluid;
enclosing the catheter and wetting fluid in a receptacle to form a closed receptacle, the receptacle having a first part and a second part;
arranging at least one sticky adhesive area on the surface of a first part of the receptacle; and
folding a second part of the receptacle over the first part in such a way that the sticky adhesive area becomes covered by the second part while maintaining the closed receptacle in a closed state,
wherein both first and second parts form a part of an internal volume enclosed by the receptacle,
the catheter is located in one of the first and second parts of the receptacle, and
the wetting fluid is located in the other of the first and second parts of the receptacle.

12. The assembly of claim 1, wherein the at least one sticky adhesive area has an extension exceeding 2 cm$^2$.

13. The assembly of claim 1, wherein the at least one sticky adhesive area has an extension exceeding 3 cm$^2$.

14. A catheter assembly comprising:
a catheter;
a closed receptacle enclosing said catheter, the receptacle having a first part and a second part, said parts being foldable over each other while the receptacle is maintained in a closed state, wherein said first part houses the catheter and said second part includes a wetting fluid compartment;
a wetting fluid located in the wetting fluid compartment; and at least one sticky adhesive area arranged on the surface of one of the first and second parts of the receptacle in such a way that the sticky adhesive area is covered by the other of the first and second parts when the receptacle is in a folded disposition, and exposed to the environment when the receptacle is in an unfolded disposition.

15. A catheter assembly comprising:

a catheter;

a closed receptacle enclosing said catheter, the receptacle having a first compartment and a second compartment separated from the first compartment by a fold line, said first and second compartments being foldable over each other at the fold line while the receptacle is maintained in a closed state, wherein said first compartment houses the catheter and further includes at least one tear line for opening the receptacle; and at least one sticky adhesive area arranged on the surface of one of the first and second compartments of the receptacle in such a way that the sticky adhesive area is covered by the other of the first and second compartments when the receptacle is in a folded disposition, and exposed to the environment when the receptacle is in an unfolded disposition.

* * * * *